United States Patent [19]

Mascioli et al.

[11] Patent Number: 4,820,731
[45] Date of Patent: Apr. 11, 1989

[54] PARENTERAL DIETARY SUPPLEMENT AND METHOD OF MINIMIZING EFFECTS OF INFECTION THROUGH DIET

[75] Inventors: Edward A. Mascioli, Cambridge; George L. Blackburn, Jamaica Plain; Bruce R. Bistrian, Ipswitch; Vigen K. Babayan, Waban, all of Mass.

[73] Assignee: New England Deaconess Hospital Corporation, Boston, Mass.

[21] Appl. No.: 207,122

[22] Filed: Jun. 15, 1988

Related U.S. Application Data

[62] Division of Ser. No. 630,732, Jul. 12, 1984, Pat. No. 4,752,618.

[51] Int. Cl.$^4$ ............................................. A61K 31/22
[52] U.S. Cl. .................................... 514/549; 514/552; 514/560; 424/95
[58] Field of Search ...................... 514/549, 552, 560; 424/95

[56] References Cited

U.S. PATENT DOCUMENTS 2,977,283  3/1961  Meyer et al. ..................... 514/547
4,101,673  7/1978  Chang ............................... 514/549

Primary Examiner—Sam Rosen
Attorney, Agent, or Firm—Lahive & Cockfield

[57] ABSTRACT

Disclosed is a method of minimizing infection and minimizing the risks of infection in at risk animals and patients. A dietary supplement to accomplish this objective is also disclosed. The method includes the step of administering a diet rich in $\omega 3$ fatty acids, for example by adding a substantial proportion of fish oils to the diet. The dietary supplement is particularly well suited to patients receiving total parenteral nutrition. A parenteral diet or diet supplement containing a mixture of oils, one rich in $\omega 3$ fatty acids and the other rich in $\omega 6$ fatty acids is disclosed.

20 Claims, No Drawings

PARENTERAL DIETARY SUPPLEMENT AND METHOD OF MINIMIZING EFFECTS OF INFECTION THROUGH DIET

ACKNOWLEDGEMENT

Funding for the research which led to this application was furnished, in part, by grant GM-30632 from the Institute of General Medical Sciences, National Institutes of Health.

This is a division of application Ser. No. 630,732, filed July 12, 1984, now U.S. Pat. No. 4,752,618.

BACKGROUND OF THE INVENTION

The present invention relates to a method of dietary control which reduces the effects of infection as well as minimizing the effects of subsequent infection in at risk animals, particularly human patients. A dietary supplement useful in the method of the invention is also disclosed.

Animals can be infected by many agents which break down the natural defenses and cause illness. These agents include bacteria, viruses, parasites, and fungi. While a great number of drugs have been developed to combat these infectious agents, the primary defense is the body's own immune system. The effectiveness of the body's defensive system against infection depends on the level of certain chemicals, e.g., prostaglandins, in the blood and cell membranes. These chemicals are synthesized from precursor molecules, e.g., fatty acids, obtained in the diet. In fact, some antiinfection drugs work by modifying the levels of synthesis of these molecules.

The amount and family of fatty acids in the diet is one of the keys to nutrition. There are three major familes of polyunsaturated fatty acids: $\omega 3$, $\omega 6$ and $\omega 9$. The names are based on the location of the closest double bond to the methyl end of the fatty acid; that is, if the closest double bond is between the third and fourth carbon atoms from the methyl group, the molecule is a $\omega 3$ fatty acid while if the double bond is between the sixth and seventh carbons, it is classified as a $\omega 6$ fatty acid. Mammals can desaturate or elongate fatty acid chains but cannot interconvert fatty acids from one family to another. The most significant fatty acids are those which have been desaturated and elongated to the twenty carbon length. The $\omega 9$ fatty acids are elongated to form eicosatrienoic acids (C20:3$\omega$9), the $\omega 6$ fatty acids form arachidonic acid (C20:4$\omega$6), and the $\omega 3$ fatty acids form eicosapentaenoic acid (C20:5$\omega$3) or docosahexaenoic acid (C22:6$\omega$3). The notation (C__:__$\omega$__) gives the number of carbons in the chain, the number of double bonds and the class of the fatty acid, respectively.

Most people in industrialized nations obtain a high proportion of their fatty acids from meat fats and vegetable oils. These fatty acid sources are high in $\omega 6$ fatty acids and low in $\omega 3$ fatty acids. Therefore, arachidonic acid is the predominant twenty carbon desaturated and elongated fatty acid in the plasma and membranes of these people. In countries where fish oil, which contains a high proportion of $\omega 3$ fatty acids, is the predominant fatty acid source, eicosapentaenoic acid is the major desaturated fatty acid found in the plasma and membranes.

Part of the significance of the twenty carbon fatty acids is their ability to act as substrates in the prostanoid synthesis pathway which forms prostaglandins from fatty acids. The first enzyme in this pathway is cyclo-oxygenase whose primary substrate in mammals is arachidonic acid. In the platelets, arachidonic acid is modified by the enzymes of the pathway to form thromboxane $A_2$, a potent platelet aggregator and vasoconstrictor. In endothelial cells, arachidonic acid forms prostacyclin $I_2$, a vasodilator and platelet antiaggregator. Both thromboxane $A_2$ and prostacycline $I_2$ are prostaglandins of the "2" series.

However, the enzyme cyclo-oxygenase can also use eicosapentaenoic acid as a substrate. In the platelets, eicosapentaenoic acid is formed into thromboxane $A_3$. Thromboxane $A_3$ is a weak vasoconstrictor but unlike thromboxane $A_2$, it will not aggregate platelets. In endothelial cells, prostacylin $I_3$, which has vasodilatory and platelet antiaggregating properties similar to prostacyclin $I_2$, is formed from eicosapentaenoic acid. Thromboxane $A_3$ and prostacyclin $I_2$ are prostaglandins of the "3" series. If docosahexaenoic acid is formed upon chain elongation and desaturation, or since it is present in fish oils, it also can be used as a substrate for cyclo-oxygenase. This also decreases the level of series "2" prostaglandin formation.

The fact that both $\omega 3$ and $\omega 6$ fatty acids can act as substrates for the prostanoid synthesis pathway led to the theory that dietary manipulation could modify the levels of type 2 and type 3 prostaglandins in the platelets and cell membranes. According to this theory, the availability of $\omega 3$ fatty acids in the die would cause a decrease in the level of type 2 prostaglandins in the plasma and membranes through competitive inhibition for the enzymes which normally use $\omega 6$ fatty acids as substrates. In one experiment on dietary manipulation, Sanders, Vickers and Haines, *Clin. Sci.* 61: 317-324 (1981), investigated the effect on blood lipids and hemostasis in healthy young men by supplementing their diet with cod liver oil, an oil rich in $\omega 3$ fatty acids. These researchers found that the ratio of $\omega 3$ to $\omega 6$ fatty acids and resulting products was increased in the platelets and erythrocyte phosphoglycerides by this diet modification.

In a series of papers by Dyerberg et al, e.g., *Am. J. Clin. Nutr* 28: 958-966 (1975), *Lancet* 2: 433-435 (1979), and *Am. J. Clin. Nutr.* 33: 2657-2661 (1970), the effects of diet high in $\omega 3$ fatty acids on heart disease were studied. The Greenland Eskimos, who have a low meat and high fish oil diet, were the test subjects. Since meat is high in $\omega 6$ fatty acids while fish oils have significant quantities of $\omega 3$ fatty acids, these studies provided a comparison between high $\omega 6$ and high $\omega 3$ diets. The Eskimos with the high $\omega 3$ fatty acid diets had significantly lower incidence of heart disease than Eskimos who had high $\omega 6$ fatty acid diets. The latter group were primarily Eskimos who had moved to Denmark and changed their diets to have a substantial proportion of $\omega 6$ fatty acids. These experiments showed that dietary manipulation could change the susceptibility to heart disease.

Some hospitalized patients, particularly critically ill patients, receive total parenteral nutrition. Since most patients receiving parenteral nutritional systems have a high risk of infection, a diet which minimizes the risk of infection would be a substantial benefit to this class of patients. Parenteral nutrition diets include a source of fatty acids since fatty acids are necessary for adequate biochemical functioning. However, standard parenteral diets use fatty acids derived primarily from soybean or safflower oil which as with most plant oils, are high in ω6 fatty acids but have little or no ω3 fatty acid content. While some ω6 fatty acids are essential to good health, somewhere between 2 and 4 percent of the total calorie content is all that is necessary. Conventional parenteral nutrition diets supply 10–15 percent, occasionally as high as 50 percent, of the calorie content as the ω6 fatty acids, a clear excess.

Lowering ω6 fatty acids may lead to an increase in platelet thromboxane $A_3$ levels. One theory for the decreased heart disease among eskimoes is that the platelets are not as "sticky" if the thromboxane $A_2$ levels are lowered. Since the production of thromboxane $A_3$ is normally at the expense of thromboxane $A_2$, a diet which lowers the ω6 fatty acid levels might lead to a decrease in heart disease.

Cook, Wise and Halushka, *J. Clin. Invest.* 65: 227 (1980) investigated the thromboxane $A_2$ levels in rats challenged with endotoxin. They found endotoxin shock increases thromboxane $A_2$ levels in the platelets. Rats treated with imidazole (a thromboxane synthetase inhibitor), indomethacin (a fatty acid cyclo-oxygenase inhibitor), or those animals with essential fatty acid deficiency (ω6 fatty acid deficiency) had higher survival rates to endotoxin shock than did normal rats. All of the groups of animals with higher survival rates exhibited lower thromboxane $A_2$ levels.

Accordingly, an object of the invention is to provide a method of minimizing the effects of infection and minimizing the effects of subsequent infection in at risk animals, particularly humans, by administering a diet which promotes resistance to infection without interfering with essential bodily processes. Another object of the invention is to provide a dietary supplement which provides sufficient nutrition in animals while reducing the risk of infection. A further object of the invention is to provide a method of treating patients, primarily patients having high risk of infection, with a dietary supplement which provides essential fatty acids while assisting in resistance to infection. These and other objects and features of the invention will be apparent from the following description.

SUMMARY OF THE INVENTION

The present invention features a method of minimizing the effects of infection and minimizing the effects of subsequent infection in at risk animals. The invention includes the step of administering a diet rich in ω3 fatty acids, preferably by administration of oils rich in ω3 fatty acids. Oils rich in ω3 fatty acids are selected from the group consisting of fish oils, e.g., herring, anchovy, cod, and menhaden oil, and various unusual plant oils. The oils may be concentrated to provide a high percentage of ω3 fatty acids per unit volume. The preferred animals for administration of the diets or humans, e.g., hospitalized patients. The patients may have an infection at the time of administration of the diet or may be members of a class having a high risk of infection. These high risk patients include those suffering with secondary immunosuppression due to chemotherapy or diabetes mellitus, protein-malnourished patients, or patients undergoing abdominal surgery. The infections may be wound infections, empyemas, bacteramias, abscesses, or septicemias. These infections are caused by a variety of infectious agents including bacteria, viruses, parasites, and fungi. The oils rich in ω3 fatty acids may be administered orally or intravenously.

The invention also features a dietary supplement having 10 to 20 percent by weight of an oily fraction rich in ω3 fatty acids, 1–2 percent by weight of an emulsifier and sterile water. The emulsifier is selected from a group consisting of egg yolk phospholipids and soybean phospholipids. The dietary supplement may also include 1–3 percent of an osmolality modifier such as glycerin. The oily fraction consists of a mixture of oils rich in ω3 fatty acids and oils rich in ω6 fatty acids, e.g., oils rich in linoleic acid. The oils rich in ω3 fatty acids provide 10–90 percent of the total fatty acids. Oils rich in ω6 fatty acids include safflower, sunflower, and soybean oils while oils rich in ω3 fatty acids include fish oils derived from herring, cod, anchovy and menhaden as well as unusual plant oils.

The invention further features a method of minimizing the effects of infection and minimizing the effects of subsequent infection in at risk patients by administration of a dietary supplement. This supplement supplies all the essential fattyy acids while providing resistance to infection by modification of the substrates for some enzyme processes. The dietary supplements of the invention is useful in this method.

DESCRIPTION

The present invention relates to a method of using dietary control to minimize infection and to minimize the risk of subsequent infection in high risk animals and patients. Mixtures of lipids-containing oils replace the standard fatty acid portion of conventional dietary supplements, e.g., those used in parenteral feedings. By substituting ω3 fatty acids for conventional ω6 fatty acids, survival to challenge with infection is improved.

Conventional dietary supplements have primarily soybean or safflower oil as their lipid or fatty acid source. Soybean oil has approximately 53 percent ω6 fatty acids and only 8 percent ω3 fatty acids while safflower oil has almost 78 percent ω6 fatty acids and substantially no ω3 fatty acids. In contrast, fish oils such as menhaden oil have 22 percent or more ω3 fatty acids and only 2–5 percent ω6 fatty acids. By replacing the predominantly ω6 fatty acid-containing oils with ω3 fatty acid-containing oils, the levels of type 2 prostaglandins is reduced and the levels of type 3 prostaglandins increased. Since infectious agents such as endotoxins increase the levels of type 2 prostaglandins, the lowering of type 2 prostaglandins by diet may improve chance of survival after challenge with these infections. For example, patients receiving parenteral dietary nutrition normally have lowered resistance due to immunosuppression. Infection is one of the major causes of complications, including death, in this type of patient. By dietary modifications, survival and full recovery are promoted.

The following non-limiting examples will show the efficacy of the present invention.

EXAMPLE 1

This Example illustrates that animals fed a diet in which the primary lipid source are oils rich in ω3 fatty acids rather than a diet containing oils rich in ω6 fatty acids promotes survival when the animals are challenged with endotoxin. The animals were healthy, male Hartley strain guinea pigs from Elm Hill Breeding Laboratories in Chelmsford, Mass. The weight of the animals at the initiation of the experiment were 200 to 250 grams. The animals were initially fed standard laboratory guinea pig chow made by Ralston-Purina Company for one week and then switched to the experimental diets.

Table 1 lists the ingredients of the diets used for both groups of guinea pigs.

TABLE 1
DIET COMPOSITION: MODIFIED REID-BRIGGS SEMI-PURIFIED GUINEA PIG DIET

| INGREDIENT | AMOUNT PER KILOGRAM (GRAMS) |
|---|---|
| Casein | 300 |
| Corn Starch | 200 |
| Sucrose | 89 |
| Glucose | 0 |
| Cellulose | 150 |
| Oil | 150 |
| Arginine | 3 |
| Salt Mix | 90 |
| Vitamin Mix | 10 |
| Choline Chloride | 4 |
| Ascorbic Acid | 4 |
| | 1000 gm total |

The diets fed to the two groups of guinea pigs were identical except the control group received 150 gm of safflower oil while the second group received 145 gm of menhaden with 5 gm of safflower oil added to prevent linoleic acid deficiency. The diets are standard Reid-Briggs guinea pig diets except that oil content is raised so the diet contains 15 percent by weight of lipid as opposed to traditional 7.3 percent. This allows 36 percent of the dietary calories to be lipid-derived as compared with the standard 15 percent. Table 8 illustrates the lipid content of safflower oil and menhaden oil.

TABLE 2
DIETARY OIL FATTY ACID COMPOSITION (IN PERCENT TOTAL FATTY ACIDS)

| FATTY ACID | SAFFLOWER OIL | MENHADEN OIL |
|---|---|---|
| C14:0 Myristic | .1 | 11.6 |
| C16:0 Palmitic | 6.5 | 13 |
| C16:1$\omega$7 Palmitoleic | | 13.3 |
| C18:0 Stearic | 2.4 | 2.1 |
| C18:1$\omega$9 Oleic | 13.1 | 6.7 |
| C18:1$\omega$7 | | 3.3 |
| C18:2$\omega$6 Linoleic | 77.7 | 1.1 |
| C20:4$\omega$6 Arachidonic | | .7 |
| C20:4$\omega$3 | | 1.9 |
| C20:5$\omega$3 Eicosapentaenoic | | 17.3 |
| C22:5$\omega$6 | | .4 |
| C22:5$\omega$3 | | 2.0 |
| C22:6$\omega$3 | | 8.2 |
| C24:1$\omega$9 | | .4 |
| Other | .2 | 18 |

The animals were kept on these diets for six weeks prior to endotoxin challenge. Each of the groups were subdivided into two groups at 6 weeks and one of the subgroups received 1 cc of a 0.9 percent saline solution while the other half received 10 mg/kg body weight of the drug ibuprofen intra-peritoneally. Ibuprofen is a cyclo-oxygenase inhibitor. One hour after administration of the saline or ibuprofen, the animals all received 0.5 mg/100 gm body weight of the endotoxin, an approximately $LD_{50}$ dosage for these animals. The endotoxin, a lipopolysaccharide derived from *E. coli*, was obtained from Difco Laboratories. A portion of the animals was retained for four days to determine survival against endotoxin while another portion was sacrificed one hour after endotoxin administration for collection of plasma. The sacrificed animals were decaptitated and the blood collected in EDTA tubes to which 25 mcg/cc ibuprofen had been added. The blood was spun down, the plasma separated and frozen for subsequent fatty aicd, thromboxane $B_2$, and 6-keto-$PGF_1$ $\alpha$ analysis.

One problem with this diet rich in $\omega 3$ fatty acids was that over the six weeks of the experiment, the control group ($\omega 6$ fatty acid rich diet) guinea pigs gained an average of 304 gms while the guinea pigs on the $\omega 3$ fatty acids rich diet gained an average of only 113 grams. By increasing the $\omega 6$ fatty acids from 2 percent to 4 percent of the total intake, this weight gain differential might be obviated.

Table 3 illustrates the survival of the two groups of guinea pigs at 12, 24, 48, and 72 hours after endotoxin challenge. While both groups show substantially equal survival at 12 hours, from 24 hours on the group fed the diet rich in $\omega 3$ fatty acids (menhaden oil) showed a threefold increase in survival.

TABLE 3
SURVIVAL FROM $LD_{50}$ ENDOTOXIN

| DIET | 12 HOURS n percent | 24 HOURS n percent | 48 HOURS n percent | 72 HOURS n percent |
|---|---|---|---|---|
| Safflower Oil (n = 30) | 16 (53) | 6 (20) | 4 (13) | 4 (13) |
| Menhaden Oil (n = 30) | 20 (67) | 18 (60) | 15 (50) | 14 (47) |

Clearly, replacing the $\omega 6$ fatty acids by $\omega 3$ fatty acids enhances survival to endotoxin shock.

Table 4 illustrates the levels of thromboxane in the $B_2$ plasma of the two groups. Thromboxane $B_2$ is a stable metabolite of thromboxane $A_2$ so it was used for the measurement because of the rapid metabolization of the thromboxane $A_2$. While it is evident from Table 4 that ibuprofen and endotoxin challenge clearly affect the thromboxane $B_2$ level, it is not clear that the diet affects the thromboxane $B_2$ level.

TABLE 4
PLASMA THROMBOXANE $B_2$ LEVELS

| DIET | IBUPROFEN | BEFORE | AFTER |
|---|---|---|---|
| Safflower Oil | no | 172 ± 26 | 451 ± 103 |
| Safflower Oil | yes | 64 ± 9 | 78 ± 13 |
| Menhaden Oil | no | 292 ± 60 | 397 ± 25 |
| Menhaden Oil | yes | 98 ± 28 | 211 ± 50 |

X ± SEM in pg/ml
N = 6 for all groups

Several explanations of these results are possible. One possibility is that survival cannot be correlated to thromboxane $A_2$ or $B_2$ levels. Second, the testing for thromboxane $B_2$ itself may cause an artifact. Measurements were made by a radioimmunoassay procedure and no studies have been done to differentiate between thromboxane $B_2$ and thromboxane $B_3$, the stable metabolite of thromboxane $A_3$. Since there is only a small structural difference between these type 2 and type 3 thromboxanes (one double bond), it is possible that there is significant cross reactivity between the thromboxanes so part of the measured thromboxane $B_2$ could actually be thromboxane $B_3$. Thromboxane $A_3$ should be produced from the $\omega 3$ fatty acids.

Table 5 shows the plasma 6-keto-$PGF_1$ $\alpha$ levels for the various groups. 6-keto-$PGF_1$ $\alpha$ is a stable metabolite of prostacyclin $I_2$.

TABLE 5
PLASMA 6-KETO-$PGF_1$ $\alpha$ LEVELS

| DIET | IBUPROFEN | ENDOTOXIN BEFORE | ENDOTOXIN AFTER |
|---|---|---|---|
| Safflower Oil | no | 43.7 ± 11.3 | 544 ± 179 |
| Safflower Oil | yes | 58.3 ± 14.0 | 71.6 ± 10.4 |
| Menhaden Oil | no | 81.0 ± 10.7 | 502 ± 167 |

TABLE 5-continued

| | | PLASMA 6-KETO-PGF$_1$ α LEVELS | |
|---|---|---|---|
| | | | ENDOTOXIN |
| DIET | IBUPROFEN | BEFORE | AFTER |
| Menhaden Oil | yes | 55.7 ± 13.5 | 138.3 ± 39.7 |

X ± SEM in pg/ml
n = 6 for all groups

As with the thromboxane B$_2$ assay, cross reactivity with Δ17-6 keto-PGF$_1$ α, the stable metabolite of prostacyclin I$_3$, was not tested. This may account for the lack of a difference in the 6-keto-PGF$_1$ α levels among the groups. Δ 17-6 keto-PGF$_1$ α is produced from ω3 fatty acids.

What is evident from this experiment is that the diet modification promoted enhanced survival of the guinea pigs fed the diet rich in ω3 fatty acids. The mechanism for enhanced survival is not clear, however.

EXAMPLE 2

This Example illustrates one procedure for forming a dietary supplement for patients which will enhance resistance to infection. Patients who may benefit from such a supplement include those with secondary immunosuppression due to diabetes mellitus or chemotherapy. In these latter patients, the total polymorphonuclear leukocyte count is normally less than 1,000/mm$^3$. Another group of patients who could benefit are protein-malnourished patients. In these patients, the serum albumin level in plasma is normally less than 3.2 gm/dl or recent weight loss of greater than 10 percent of original body weight has occurred.

The oil emulsion is made as follows. For each liter of emulsion, 100–200 gm of refined and bleached oil rich in ω3 fatty acids is mixed with 11 gms of an emulsifier, e.g., egg yolk phospholipids USP, 22.5 gms. of an osmolality modifier, e.g., glycerin USP, and sterile water USP to bring the volume to a liter. Specifically, the oil is added to a high shear mixer such as a Waring mixer with steel blades operated at 1,600 RPM. The phospholipids are added slowly to the oil and mixed at high speed for 6 minutes. Eight hundred milliliters of sterile water is added in a steady stream to the phospholipid and oil mixture and emulsified for 20 minutes at 1600 RPM. The attainment of the oil-in-water emulsion is confirmed by the "drop dispersion test." Emulsification is continued until the coarse oil emulsion disperse freely in water but not in oil.

The coarse emulsion is then passed through a high speed homogenizer five times until particle size is less than 1 micron. At that time, five more passes through the high speed homogenizer are performed and with each pass, glycerin is added to the emulsion. During the last five passes, additional water is added to make the final emulsion volume up to the one liter batch. Normally, all volumes are multiplied ten-fold and a ten liter batch is mixed at once.

Aliquots of the emulsion are set aside for measuring particle size which should be between 0.24 and 0.75 microns. The solutions are then passed through a five micron particle filter into sterile and pyrogen free evacuated containers The emulsion is then sterilized at low temperature (105° C.) for 25 minutes. The solutions are cooled to room temperature and stored in the dark at 9° C. for one week. Prior to patient administration, the samples are retested for particle size and the presence of bacterial or endotoxin contamination. If the particle size is greater than 1 micron or the endotoxin concentration is greater than 1 ng, the batch of emulsion is discarded.

As previously noted, this dietary supplement can be used in patients who may be susceptible to a number of infectious agents. Examples of these infectious agents include *E. coli*, Pseudomonas, or Klebisiella for the gram negative bacteria, *Staphylococcus aureus* or *albus* for the gram positive bacteria, *Herpes simplex* or *zoster* for the viruses, and fungi such as Candida. A variety of parasites can also be controlled by this type of supplement.

While the method and dietary supplement disclosed herein will not necessarily prevent the onset of infection caused by these agents, it will promote survival of infected patients or animals. The specific method and dietary supplement set forth herein are purely illustrative and those skilled in the art may determine other modifications and variations of these procedures. Such other modifications and variations are included within the scope of the following claims.

What is claimed is:

1. A dietary supplement for parenteral administration comprising:
  at least 10% by weight of an oily fraction formed of a mixture of oils selected from a group consisting of oils which have ω6 fatty acids as their primary fatty acids and oils which have ω3 fattyy acids as their primary fatty acids, said oils having ω3 fatty acids as their primary fatty acids forming 10–90% by weight of said oily fraction;
  1–2% by weight emulsifier; and
  sterile water.

2. The dietary supplement of claim 1 wherein said emulsifier is selected from a group consisting of egg yolk phospholipids and soybean phospholipids.

3. The dietary supplement of claim 2 wherein said dietary supplement further comprises 1–3 percent by weight of an osmolality modifier.

4. The dietary supplement of claim 3 wherein said osmolality modifier comprises glycerin.

5. The dietary supplement of claim 1 wherein said oils which have ω6 fatty acids as their primary fatty acids comprise oils having linoleic acid as their primary ω6 fatty acid.

6. The dietary supplement of claim 5 wherein said oils having linoleic acid as their primary ω6 fatty acid are selected from a group consisting of safflower, sunflower and soybean oils.

7. The dietary supplement of claim 1 wherein said oils having ω3 fatty acids as their primary fatty acid source cmprise fish oils.

8. The dietary supplement of claim 7 wherein said fish oils are selected from a group consisting of oils derived from herring, anchovy, and menhaden.

9. The dietary supplement of claim 1 wherein said oily fraction comprises 10–20% by weight of said dietary supplement.

10. The dietary supplement of claim 1 wherein said oils having 107 3 fatty acids as their primary fatty acids comprise concentrated ω3 fatty acid containing oils.

11. A diety for total parenteral nutrition comprising:
  at least 10% by weight of an oily fraction formed of a mixture of oils selected from a group consisting of oils which have Ω6 fatty acids as their primary fatty acids and oils which have ω3 fatty acids as their primary fatty acids, said oils having ω3 fatty acids as their primary fatty acids forming 10–90% by weight of said oily fraction;

1-2% by weight emulsifier; and
sterile water.

12. The diet for total parenteral nutrition of claim 11 wherein said emulsifier is selected from a group consisting of egg yolk phospholipids and soybean phospholipids.

13. The diet for total parenteral nutrition of claim 11 further comprising 1-3% by weight of an osmolality modifier.

14. The diet for total parenteral nutrition of claim 13 wherein said osmolality modifier comprises glycerin.

15. The diet for total parenteral nutrition of claim 11 wherein said oils which have ω6 fatty acids as their primary fatty acid comprise oils having linoleic acid as their primary ω6 fatty acid.

16. The diet for total parenteral nutrition of claim 15 wherein said oils having linoleic acid as their primary ω6 fatty acid are selected from a group consisting of safflower, sunflower and soybean oils.

17. The diet for total parenteral nutrition of claim 11 wherein said oils having ω3 fatty acids as their primary fatty acids comprise fish oils.

18. The diet for total parenteral nutrition of claim 17 wherein said fish oils are selected from a group consisting of oils derived from herring, anchovy, and menhaden.

19. The diet for total parenteral nutrition of claim 11 wherein said oily fraction comprises 10-20% by weight of said dietary supplement.

20. The diet for total parenteral nutrition of claim 11 wherein said oils having ω3 fatty acids as their primary fatty acids comprise concentrated ω3 fatty acid containing oils.

* * * * *

UNITED STATES PATENT AND TRADEMARK OFFICE
CERTIFICATE OF CORRECTION

PATENT NO. : 4,820,731
DATED : April 11, 1989
INVENTOR(S) : Mascioli et al.

It is certified that error appears in the above-identified patent and that said Letters Patent is hereby corrected as shown below:

At Column 8, line 51, delete "cmprise" and insert --comprise--.

At Column 8, line 59, delete "107 3" and insert --$\omega 3$--.

At Column 8, line 61, delete "A diety" and insert --A diet--.

Signed and Sealed this

Thirtieth Day of January, 1990

Attest:

JEFFREY M. SAMUELS

Attesting Officer     Acting Commissioner of Patents and Trademarks